US005504196A

United States Patent [19]

Clarke Garegg et al.

[11] Patent Number: 5,504,196

[45] Date of Patent: Apr. 2, 1996

[54] REMOVAL OF COLOR, POLYSACCHARIDES, PHENOLICS AND TURBIDITY FROM SUGAR-CONTAINING SOLUTIONS AND DERIVATED FIBROUS RESIDUES THEREFORE

[76] Inventors: Margaret A. Clarke Garegg; Earl J. Roberts, both of 1100 Robert E. Lee Blvd., New Orleans, La. 70124

[21] Appl. No.: 117,712

[22] Filed: Sep. 8, 1993

[51] Int. Cl.[6] .............................. C07H 15/00; C07H 1/00; C08B 30/00; C13J 1/06

[52] U.S. Cl. .............................. 536/17.2; 127/34; 127/42; 127/46.1; 127/48; 127/53; 424/195.1; 536/18.5; 536/56; 536/84; 536/123.1

[58] Field of Search .............................. 536/127, 18.5, 536/17.2, 123.1, 56, 84; 514/53; 424/195.1; 127/34, 42, 46.1, 48, 53

[56] References Cited

U.S. PATENT DOCUMENTS

| | | | |
|---|---|---|---|
| 4,076,552 | 2/1978 | Farag et al. | 127/50 |
| 4,196,017 | 4/1980 | Melville et al. | 127/41 |
| 4,507,472 | 3/1985 | Usher et al. | 536/51 |
| 4,746,368 | 5/1988 | Frank et al. | 127/55 |
| 4,818,598 | 4/1989 | Wong | 242/284 |

FOREIGN PATENT DOCUMENTS

| | | |
|---|---|---|
| 270904 | 11/1991 | Czechoslovakia . |
| 0406837 | 1/1991 | European Pat. Off. . |
| 06065162 | 8/1994 | Japan . |
| 4586 | of 1878 | United Kingdom . |

OTHER PUBLICATIONS

Roberts et al. *Canadian J. of Chemistry*, vol. 45, pp. 261–265, (1967).

J. Hradil, et al, Chem. Abst. 117:153116b, 1992.

Roberts et al., Chem Abst 199:162739a 1993.

Von O. Bobleter et al., "Anion Exchangers Based on Wood or Cellulose for the Decontamination . . . ", Atomkernenergie 8(11) (1963), pp. 415–418.

L. Ya. Petrova et al., "Preparation of Powdered Cellulose and Ion–Exchanging Materials . . . ", Inst. Fiz Khim. (1965), pp. 270–274.

*Primary Examiner*—Douglas W. Robinson
*Assistant Examiner*—Howard C. Lee
*Attorney, Agent, or Firm*—Richard W. Hanes

[57] ABSTRACT

Unwanted color and turbidity are removed from sugar solutions during the processing of raw sugar by the use of bagasse treated with a dialkylaminoalkyl compound in a basic aqueous medium, and with regenerated treated bagasse, including sugarcane bagasse, corn cobs, peanut shells, wheat straw, oat straw, barley straw, rice straw, rice hulls, cottonseed hulls and paper from wood or cotton or mixtures of the foregoing.

8 Claims, 1 Drawing Sheet

REMOVAL OF COLOR, POLYSACCHARIDES, PHENOLICS AND TURBIDITY FROM SUGAR-CONTAINING SOLUTIONS AND DERIVATED FIBROUS RESIDUES THEREFORE

FIELD OF THE INVENTION

The present invention relates to sugar manufacturing and refining processes and more particularly to compositions and processes for decolorizing and removing turbidity from aqueous solutions containing sugar.

BACKGROUND OF THE INVENTION

In conventional processes for the production of sugar from sugar cane and sugar beet, the removal of color, turbidity and suspended solids from aqueous solutions (juices, syrups or liquors) is an important step in the recovery of refined, substantially color-free sugar from the processes. A wide variety of process variations have been employed in the past to achieve this desired result. Typical sugarcane and sugarbeet manufacturing and refining processes are described in Cane Sugar Handbook, 22th edition, G. P. Meade and J. C. P. Chen, eds, Wiley-Interscience, New York, 1985, 1134 pp. and Beet Sugar Technology, 3rd edition, R. A. McGinnis, Ed., Beet Sugar Development Foundation, Denver, Colo., 1982, 855 pp., all of which are incorporated herein by reference, in their entirety.

OBJECTS OF THE INVENTION

It is an object of the present invention to provide an alternative economical process to those currently employed for removing unwanted color, turbidity and suspended solids in any type of sugar manufacture including the manufacture of raw cane sugar and beet sugar.

It is a further object of the present invention to provide novel compositions and a method for their production which will accomplish the foregoing objective.

SUMMARY OF THE INVENTION

It has been discovered that certain fibrous plant residues such as sugar cane bagasse can be reacted in a particular manner with certain dialkyl-aminoalkyl chloride hydrochlorides to form derivatives which can be used to remove color, colorant precursors turbidity and suspended and collodial solids from aqueous solutions in the manufacture of sugar in the manufacture of sugar.

DETAILED DESCRIPTION OF THE INVENTION

Diethylaminoethyl chloride reacts with polysaccharides in the presence of base to form stable compounds through an ether linkage. Some of the compositions produced by this reaction have been useful in the wet formation of papers and as chromatographic supports.

Reducing the color, turbidity and the suspended and collodial solids has been a necessary step in the manufacture of sugar. Sugarcane bagasse, a fibrous by-product of the sugar manufacturing process is readily available and an economically attractive starting material for use in sugar processing.

It has been discovered that in particular the reaction of diethylamino-ethyl chloride obtained from its hydrochloride, with sugarcane bagasse in a basic aqueous reaction with the sugarcane bagasse produces a complex which is highly effective in removing color, turbidity and suspended and collodial solids from sugar-containing solutions.

Preparation of DEAE-bagasse

Figure 1:
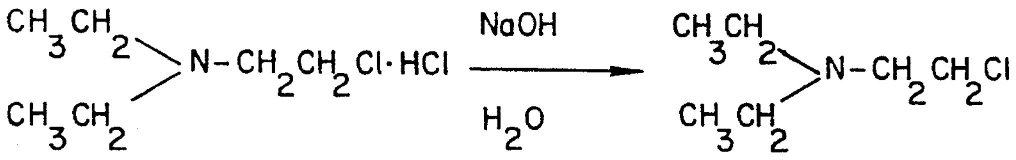
FIG. 1 is a chemical equation empirically showing the aqueous based reaction between diethylaminoethyl chloride hydrochloride and sodium hydroxide.
Figure 2:
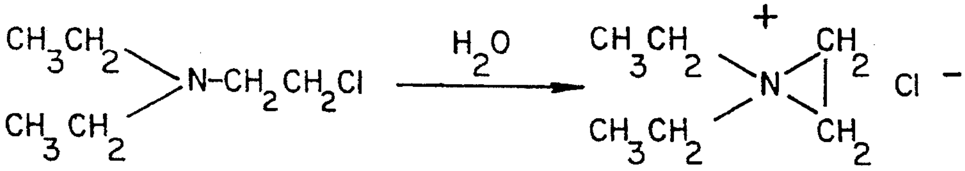
FIG. 2 is a chemical equation showing the reaction between the diethylaminoethyl chloride obtained in FIG. 1 and water.
Figure 3:
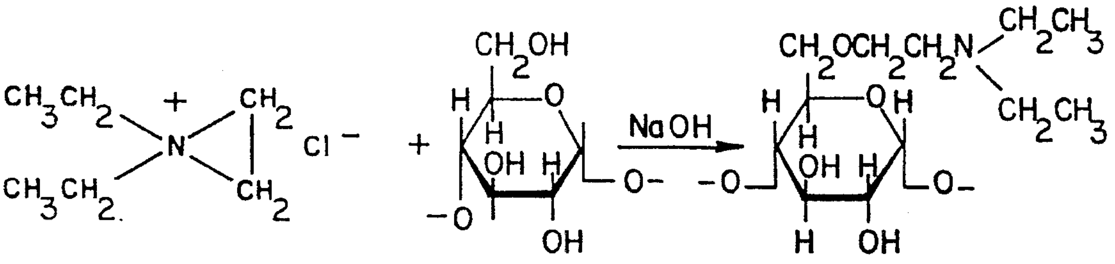
FIG. 3 is a representative chemical equation showing the aqueous based reaction between the product of the reaction shown in FIG. 2 and a glucose unit of cellulose.

Whole bagasse or other fibrous residues of corn cobs, wheat straw, oat straw, barley straw, rice hulls, cottonseed hulls, peanut hulls or paper, (30 g), ground to pass a 20 mesh screen was suspended in 500 ml of water. Sodium hydroxide (10 g) was added. The mixture was stirred and when the sodium hydroxide was dissolved 10 g of DEAE chloride hydrochloride were added and the mixture heated to 90° C. It was then allowed to cool and 10 g of sodium hydroxide and 10 g of DEAE chloride hydrochloride were added and the mixture was again heated to 90° C. The mixture was allowed to cool, and 10 g DEAE chloride hydrochloride were added, and the mixture was again heated to 90° C. The mixture was then filtered with suction and the insoluble material was washed with water until no more color was removed. The DEAE complexed bagasse was air dried. The yield was 22 g. The reactions for the cellulose part of the bagasse are shown in FIGS. 1–3. Similar reactions take place with the hemicellulose fractions of bagasse.

Regeneration of DEAE-bagasse

After several hours of continuous decolorization treatments or up to twenty batch treatments, the DEAE-bagasse complex was regenerated with 5% sodium chloride solution, approximately 100 ml to 10 g bagasse, in a single pass followed by water washing (100 ml).

EXAMPLES

Example I

Batchwise decolorization with DEAE-bagasse

Five 100 g batches of 25 Brix solutions of a single raw sugar were prepared.

DEAE-bagasse, 2 g, ground to pass a 20 mesh screen and containing 1.23% by weight nitrogen (by elemental analysis) was added to one solution and stirred for 5 minutes. The DEAE-bagasse was filtered off and was regenerated by washing with 5% NaCl solution and reused. The same 2 g of DEAE-bagasse was used to decolorize all five samples. Colors of the treated solutions and color of the original were measured at pH 7. The results are shown in Table 1.

TABLE 1

| Color removed from raw sugar by single batch treatment | | |
|---|---|---|
| Sample | ICU | % color removed |
| Original solution | 6419 | — |
| Treated solutions | | |
| 1 | 979 | 85 |
| 2 | 958 | 85 |
| 3 | 964 | 85 |
| 4 | 915 | 86 |
| 5 | 878 | 86 |
| Average color removal | | 85.6 |

Example II

Column decolorization with DEAE-bagasse, single pass

A column, (48 mm i.d., 60 mm b.d. depth) was prepared containing 10 g of DEAE-bagasse which had been ground to pass a 20 mesh screen and containing 1.17% by weight of nitrogen. Several 100 g samples of 40 brix solutions of different raw sugars were passed through the column. The column was regenerated with 100 ml of 5% sodium chloride after the passage of each sugar solution. The color in the effluents along with that in the original solutions was measured. It was found that the DEAE-bagasse removed 85% to 90% of the color and the solutions contained no visible turbidity. The DEAE-bagasse was therefore shown to have removed most of the color from raw sugar solutions; its durability under repeated use was then tested. Twenty (100 g, 40 Bx) solutions of a raw sugar were passed through the column as described above followed by 200 ml of water. The column was regenerated after the passage of each solution. The color in the effluents, 200 ml from each sample, along with the original solution were measured at pH 7.0. None of the effluents contained any visible turbidity. The results are shown in Table 2.

TABLE 2

| Decolorization of repeat (2) batches on DEAE-bagasse column | | |
|---|---|---|
| Sample No. | ICU | % color removed |
| Original | 2478 | — |
| 1. | 492 | 80 |
| 2. | 324 | 87 |
| 3. | 304 | 88 |
| 4. | 306 | 88 |
| 5. | 287 | 89 |
| 6. | 338 | 86 |
| 7. | 307 | 87 |
| 8. | 295 | 88 |
| 9. | 337 | 86 |
| 10. | 322 | 87 |
| 11. | 300 | 85 |
| 12. | 369 | 85 |
| 13. | 356 | 85 |
| 14. | 350 | 86 |
| 15. | 367 | 85 |
| 16. | 338 | 86 |
| 17. | 307 | 87 |
| 18. | 337 | 86 |
| 19. | 356 | 86 |
| 20. | 362 | 85 |

Example III

Turbidity removed from raw sugars

Ten 100 g batches of 40 Brix solutions of different raw sugars were passed through the column of Example II. Color and turbidity were determined in the original solutions and the effluents. The results are shown in Table 3.

TABLE 3

| Turbidity and color removal. | | | | | |
|---|---|---|---|---|---|
| Sample No. | | Color ICU | % Color removed | Turbidity ICU | Turbidity removed |
| 1. | Original | 5384 | | 2073 | |
| | Column effluent | 368 | 93 | 85 | 95 |
| 2. | Original | 3612 | | 1604 | |
| | Column effluent | 462 | 88 | 32 | 98 |
| 3. | Original | 5595 | | 1514 | |
| | Column effluent | 557 | 90 | 97 | 93 |
| 4. | Original | 3422 | | 1509 | |
| | Column effluent | 576 | 83 | 122 | 92 |
| 5. | Original | 5339 | | 1488 | |
| | Column effluent | 586 | 89 | 55 | 96 |
| 6. | Original | 8491 | | 9683 | |
| | Column effluent | 1560 | 81 | 213 | 97 |
| 7. | Original | 3359 | | 590 | |
| | Column effluent | 470 | 86 | 62 | 89 |
| 8. | Original | 4112 | | 1092 | |
| | Column effluent | 445 | 89 | 101 | 91 |
| 9. | Original | 7949 | | 1130 | |
| | Column effluent | 502 | 90 | 73 | 94 |
| 10. | Original | 5230 | | 1588 | |
| | Column effluent | 579 | 88 | 60 | 95 |

Five 100 g batches of 40 Brix solutions of the same sugar were passed through the column in Example II in succession, without regeneration. The color and turbidity in the original solution and each 200 ml effluent were determined. The results are shown in Table 4.

TABLE 4

| Turbidity and color removal, multiple pass. | | | | |
|---|---|---|---|---|
| Run No. | Color ICU | % color removed | Turbidity ICU | % Turbidity removed |
| Original | 6827 | | 1488 | |
| 1 | 586 | 92 | 55 | 96 |
| 2 | 1302 | 80 | 119 | 92 |
| 3 | 1328 | 80 | 105 | 92 |
| 4 | 1847 | 73 | 107 | 92 |
| 5 | 2277 | 67 | 214 | 85 |

Example IV

Column decolorization, multiple pass Five 100 g of 40 Brix raw sugar solution were passed through the column in Example II in succession without regeneration to determine the capacity of the DEAE-bagasse for removing color. The colors of the turbidity free effluents were measured along with that of the original solution. The results are shown in Table 5.

TABLE 5

| Column decolorization, by DEAE-bagasse, multiple pass. | | |
|---|---|---|
| Run No. | ICU | % color removed |
| Original solution | 2478 | — |
| 1 | 262 | 89 |
| 2 | 572 | 76 |
| 3 | 944 | 62 |
| 4 | 1106 | 55 |

TABLE 5-continued

| Column decolorization, by DEAE-bagasse, multiple pass. | | |
|---|---|---|
| Run No. | ICU | % color removed |
| 5 | 1204 | 50 |

Example V

Column decolorization, single pass, color components, and precursors and polysaccharide removal One hundred (100 g) grams of 40 Brix solutions of five raw sugars were passed through the DEAE-bagasse column described in Example II. The column was operated under gravity flow at the rate of 20 ml per minute. The effluents from the column along with the original solutions were analyzed for phenolics, dextran and total polysaccharides. The results are summarized in Table 6.

Phenolics indicates a group of sugar colorant precursor compounds.

TABLE 6

Removal of non-sugars by DEAE-bagasse columns.

| | Sample | Phenolics PPM | Dextran PPM | Total P'sacc. PPM |
|---|---|---|---|---|
| 1. | Raw | 896 | 339 | 1340 |
| | Column effluent | 352 (60)* | 161 (53)* | 564 (58)* |
| 2. | Raw | 447 | 430 | 1805 |
| | Column effluent | 175 (61)* | 291 (32)* | 751 (58)* |
| 3. | Raw | 988 | 520 | 2599 |
| | Column effluent | 352 (64)* | 145 (72)* | 1116 (57)* |
| 4. | Raw | 641 | 368 | 1118 |
| | Column effluent | 227 (64)* | 109 (70)* | 497 (58)* |
| 5. | Raw | 696 | 224 | 1137 |
| | Column effluent | 232 (66)* | — | 622 (46)* |

*Indicates percent removed by DEAE-bagasse

Example VI

Column decolorization; large size, heat-jacketed column

A jacketed column containing 20 g of DEAE-bagasse, ground to pass a 20 mesh screen and containing 1.11% by weight nitrogen was prepared. The DEAE-bagasse bed was 60 mm in diameter and 90 mm deep. A sample (500 g, 40 Bx) of raw sugar solution was heated to 80° C. and passed through the column under gravity flow while maintaining the temperature at 80° C. The flow rate was 20 ml per minute. The effluent was collected in 100 ml fractions and the color in each fraction along with that in the original sample was determined. The results are shown in the Table 7.

TABLE 7

Decolorization by jacketed pressurized column at 80° C.

| Fraction No. | ICU | % color removed |
|---|---|---|
| Original solution | 2826 | — |
| 3 | 181 | 93 |
| 4 | 194 | 93 |
| 5 | 311 | 89 |
| 6 | 420 | 85 |
| 7 | 569 | 80 |
| 8 | 736 | 74 |
| 9 | 932 | 67 |
| 10 | 1011 | 64 |

Example VII

Column decolorization under pressure, refinery liquors

A column was prepared containing 50 g of DEAE-bagasse which was ground to pass a 20 mesh screen and which contained 1.3% by weight nitrogen the bed of DEAE-bagasse was 3 inches in diameter and 3½ inches deep. A 1000 g (80 ml) quantity of 60 Brix solutions each of raw sugar, melted washed raw sugar, clarified liquor, remelt liquor, and clarified remelt liquor were each heated to 80° C. and was passed through the column maintained at 80° C. The column was regenerated after the passage of each solution. The flow rate was 20 ml per minute under 2 pounds of pressure. The color in each effluent (1600 ml) along with that in each original solution was determined. The results are shown in Table 8.

TABLE 8

Column decolorization, refinery liquors.

| Sample | ICU | % color removed |
|---|---|---|
| Raw sugar | 4798 | — |
| Column effluent | 540 | 85 |
| Melted washed raw sugar | 1197 | — |
| Column effluent | 90 | 92 |
| Clarified liquor | 1155 | — |
| Column effluent | 278 | 72 |
| Remelt liquor | 5302 | — |
| Column effluent | 1206 | 77 |
| Clarified remelt liquor | 3904 | — |
| Column effluent | 1075 | 72 |

Example VIII

Pilot scale column decolorization, sugarcane juice

A heat-jacketed column was prepared with 60 cubic inches DEAE-bagasse (bagasse ground to pass a 20 mesh screen), and put in an auxiliary line on clarified sugarcane juice in a sugarcane factory. The column was operated at a temperature of 80° C., and a pressure of between 3–5 psi gauge. A volume of 200 gal cane juice from milled sugarcane, was passed from milled sugar cane, (14–16 Bx, total solids, and 10%–12% sucrose) over the column at a rate of 30 gal per hour. Color, dextran and total polysaccharide removal are shown in Table 9.

TABLE 9

| Color, dextran, polysaccharide removal in pilot test | | | | |
|---|---|---|---|---|
| Time column Turbidity in service, hours | Color % removed | Dextran % removed | Total polysac. % removed | Turbidity % removed |
| 0.25 | 29 | NA | 15 | 90 |
| 0.5 | 11 | 22 | 5.0 | 46 |
| 1.0 | 79 | 33 | 23 | 50 |
| 1.5 | 22 | 58 | 6.0 | 84 |
| 2 | 23 | 21 | — | 61 |

Example IX

Removal of color precursors

Sugarcane juice (100 ml) (at about 15 Bx from fresh sugarcane) was treated with 2 g DEAE-bagasse in filtration batch process, as in Example I. The treated juice was heated and evaporated (rotary evaporator under vacuum) to syrup and then to crystallization. Color precursor compound normally present in untreated juice, form dark colored compounds during evaporation and crystallization which are incorporated into the raw sugar crystals. Sugar crystals were removed from mother liquor by filtration, and their color content measured. A second 100 ml batch of juice, not treated with DEAE-bagasse, was similarly evaporated to crystallization. Colors of juices and crystalline sugars, with and without DEAE-bagasse treatment, are shown in Table 10.

TABLE 10

| Removal of color precursors | | |
|---|---|---|
| Sample | Color (ICU) | % color reduction from DEAE-bagasse treatment |
| Sugar from untreated juice | 8,988 | |
| Sugar from treated juice | 4,295 | 52% |
| Molasses from untreated juice | 114,256 | |
| Molasses from treated juice | 17,480 | 84% |

The lower percentage of color removal in cane juice when treated before evaporation than on treatment of raw sugar supports the observation that color precursors are removed in juice.

The color removal in cane juice is lower than percentage of color removal in raw sugar, because DEAE is removing precursors from cane juice and in raw sugar the precursors have been converted to color.

In FIG. 1 the sodium hydroxide neutralizes the hydrochloric acid forming the DEAE chloride free base. This is a liquid and is insoluble in water but when stirred in water it rearranges to water soluble diethylaziridinium chloride as shown in FIG. 2. This form of the reagent is ionic and is highly reactive to hydroxyl groups in the presence of base. The reaction occurs principally at the 6-O-hydroxyl group, of the glucose units. Sugarcane bagasse is 40% to 60% cellulose, dry basis. The remainder is principally xylan and the lower molecular weight fraction is dissolved by the sodium hydroxide during the reaction. This accounts for the yield of 60% to 70% in the preparation of DEAE bagasse. The DEAE-ether linkages are very stable and can only be removed under extreme conditions.

DEAE bagasse is an anion exchanger and swells when placed in water. For this reason it should be stirred in water for 20 to 30 minutes before pouring a column. In order for it to be effective in removing color and turbidity it should contain a minimum of 0.8% nitrogen.

The color removed from the sugar solutions reported ranged from 72% to 95%. None of the effluents contained any visible turbidity, as indicated in Table 4. Color removed from sugarcane juice varied from 11% to 79%, depending on ratio of colored and non-colored precursors present.

The small amount of color not removed on DEAE bagasse was analyzed by gel permeation chromatography and shown to be low molecular weight, approximately 30,000 daltons. Colorant of this lower molecular weight range is less likely to be occluded in the crystal. All of the very high molecular weight color ($2\times10^6$ daltons) and 90%–95% of the major colorant at least 50,000 daltons, are removed from melt liquor by DEAE bagasse. The very high molecular weight fraction is difficult to remove by other adsorbents. The color adsorbed on the DEAE bagasse cannot be washed off with water, but a 5% solution of chloride, as sodium chloride, displaces the color and subsequent washing with water prepares the DEAE-Bagasse for reuse. Repeated use of the DEAE bagasse does not affect its ability to remove color. The mode of action of this material in removing sugar colorants is apparently not a simple ion exchange reaction, but possibly a combination of ion exchange and gel permeation. The removal of turbidity is apparently accomplished by physical adsorption. Many of the suspended particles are charged, and so able to be adsorbed on the negatively charged, or negatively polarized, DEAE sites. No significant ash removal has been observed indicating that removal of turbidity is by adsorption and not by ion exchange.

From the foregoing Examples and other experimental work an elemental analysis showed that the carbon content of the complex should be in the range of from about 46% by weight to about 50% by weight, and the oxygen content from about 40% by weight to about 43% by weight. The nitrogen content should be from about 0.8% by weight to about 1.5% by weight and the hydrogen content from about 5.5% by weight to about 7.5% by weight.

The foregoing description and examples are merely exemplary of the scope of the present invention. The invention relates generally to the use of substituted tertiary aminoalkyl derivatives of plant fibrous residues which can include sugarcane bagasse, corncobs, wheat straw, oat straw, rice straw, barley straw, rice hulls, cottonseed hulls, peanut hulls and paper from wood hulls or cotton. The novel complexes produced by the reaction of the tertiary aminoalkyl compounds, including N, N-diethyl aminoethyl salts with the described fibrous residues are highly effective in removing color, colorant compounds, color precursor compounds, turbidity and suspended and colloidal solids from sugar containing solutions including sugarcane and sugarbeet juices and syrups and molasses, fruit juices and syrups, and intermediate solutions in wine and beer production. Further, the desired properties can also be obtained from previously used DEAE-bagasse or other complexed fibrous plant residues by regeneration with salt-containing solutions, preferably sodium chloride.

It has also been discovered that the most preferred complex of DEAE and sugarcane bagasse will contain a minimum of about 0.8% by weight of nitrogen in its composition to be effective.

The invention has been described with respect to preferred modes of operation; however, the scope of the invention is not to be limited thereto but only by the scope of the claims in view of the applicable prior art.

We claim:

1. A process for decolorizing sugar-containing solutions comprising the steps of:

a) contacting the sugar-containing solutions with a fibrous plant residue having glucose units which has been reacted in an aqueous medium with a dialkylaminoalkyl compound in a basic aqueous medium having a pH greater than 7 to form a complex therewith having an ether linkage between the glucose unit of the plant residue and the dialkylaminoalkyl compound, and b) recovering the decolorized sugar-containing solution.

2. The process of claim 1, wherein the dialkylaminoalkyl compound is the hydrochloride of N,N-diethylaminoethyl chloride.

3. The process of claim 1, wherein the plant residue is selected from the group consisting of sugarcane bagasse, corn cobs, peanut shells, wheat straw, oat straw, barley straw, rice straw, rice hulls, cottonseed hulls and paper from wood or cotton, and mixtures thereof.

4. The process of claim 1, wherein the fibrous plant residue which has been reacted with a dialkylaminoethyl salt to form a complex therewith is regenerated after use and before subsequent use by the step of contacting said fibrous plant residue complex with a salt containing aqueous regeneration solution.

5. The process of claim 4, wherein the regeneration solution contains sodium chloride.

6. The process of claim 1, wherein the starting dialkylaminoalkyl compound is a chloride-hydrochloride.

7. The process of claim 2, wherein the complex of plant residue formed with N,N-diethylaminoethyl chloride contains at least 0.8% by weight of elemental nitrogen.

8. The process of claim 2, wherein the plant residue is sugarcane bagasse.

* * * * *